United States Patent [19]
Chen

[11] Patent Number: 6,053,483
[45] Date of Patent: Apr. 25, 2000

[54] AROMA DIFFUSER

[75] Inventor: Cheng-Chang Chen, Taipei Hsien, Taiwan

[73] Assignee: Bobson Hygiene International Inc., Taipei Hsien, Taiwan

[21] Appl. No.: 09/108,746

[22] Filed: Jul. 1, 1998

[51] Int. Cl.⁷ ...................................................... B01F 3/04
[52] U.S. Cl. .................... 261/30; 261/104; 261/DIG. 17; 261/DIG. 65; 422/124
[58] Field of Search ................................ 261/26, 30, 104, 261/107, DIG. 17, DIG. 65; 422/124

[56] References Cited

U.S. PATENT DOCUMENTS

| | | | |
|---|---|---|---|
| 4,830,791 | 5/1989 | Muderlak et al. | 261/DIG. 65 |
| 4,840,770 | 6/1989 | Walz et al. | 261/DIG. 65 |
| 4,931,258 | 6/1990 | Zlotnik et al. | 422/124 |
| 5,223,182 | 6/1993 | Steiner et al. | 422/124 |
| 5,431,885 | 7/1995 | Zlotnik et al. | 422/124 |

*Primary Examiner*—David A. Simmons
*Assistant Examiner*—Robert A. Hopkins
*Attorney, Agent, or Firm*—Sughrue, Mion, Zinn, Macpeak & Seas, PLLC

[57] ABSTRACT

An aroma diffuser includes a housing with front and rear housing parts, a circuit-mounting frame and a fan unit. The front housing part has an upper portion formed with an air outlet. The lower portion of a rear wall of the rear housing part has a carrier that extends transversely into the housing and that supports an aromatic preparation thereon. The circuit-mounting frame is disposed inside the housing and is mounted on the upper portion of the rear wall. The fan unit includes a tubular collecting wall mounted on the circuit-mounting frame and disposed above the carrier. The tubular collecting wall has upper and lower wall portions. The upper wall portion has a front side formed with a radial air flow outlet that is registered with the air outlet of the front housing part. The lower wall portion has a fan device mounted therein and controlled by a control circuit on the circuit-mounting frame so as to draw aroma of the aromatic preparation on the carrier into the tubular collecting wall and so as to blow the aroma inside the tubular collecting wall out of the air outlet of the housing via the radial air flow outlet.

6 Claims, 5 Drawing Sheets

AROMA DIFFUSER

BACKGROUND OF THE INVENTION

1. Field of the Invention

The invention relates to an aroma diffuser, more particularly to an aroma diffuser that is capable of effectively diffusing aroma within a relatively broad area and that has detachable components to facilitate maintenance and repair.

2. Description of the Related Art

Referring to FIG. 1, a conventional aroma diffuser is shown to comprise a housing 10 having front and rear housing parts 100, 101. The front housing part 100 has an upper portion formed with an air outlet 11. A carrier 12 extends transversely into the housing 10 from a lower portion of the rear housing part 101, and is capable of supporting an aromatic preparation 20 thereon. A circuit-mounting frame 13 is mounted fixedly inside the housing 10 on an upper portion of the rear housing part 101. Thus, the circuit-mounting frame 13 is disposed above the carrier 12. A sensing unit 14 is mounted on a front side of the circuit-mounting frame 13. A fan unit 15 is mounted on a bottom side of the circuit-mounting frame 13, and is disposed adjacent to the air outlet 11. A control circuit (not shown) is mounted on the circuit-mounting frame 13, and is connected electrically to the sensing unit 14 and the fan unit 15. In response to signals from the sensing unit 14, the control circuit activates the fan unit 15 so that the aroma of the aromatic preparation 20 can be blown out of the housing 10 via the air outlet 11 in order to generate a fragrant scent at the vicinity of the aroma diffuser.

In the conventional aroma diffuser, because the fan unit 15 and the aromatic preparation 20 are disposed respectively in the upper and lower portions of the housing 10, and due to the lack of a guide for guiding the aroma from the aromatic preparation 20 to the fan unit 15, the concentration of the aroma that can be diffused is relatively low, thereby limiting the effective scope of the aroma diffuser. Moreover, because most of the components of the aroma diffuser are fixed to the housing 10, maintenance and repair of the conventional aroma diffuser is inconvenient to conduct.

SUMMARY OF THE INVENTION

Therefore, the main object of the present invention is to provide an aroma diffuser that is capable of effectively diffusing aroma within a relatively broad area.

Another object of the present invention is to provide an aroma diffuser that has detachable components to facilitate maintenance and repair.

Accordingly, the aroma diffuser of this invention comprises a housing, a circuit-mounting frame and a fan unit.

The housing includes front and rear housing parts. The front housing part has an upper portion formed with an air outlet. The rear housing part has a rear wall with an upper portion and a lower portion. The lower portion of the rear wall has a carrier that extends transversely into the housing and that is adapted to support an aromatic preparation thereon.

The circuit-mounting frame is disposed inside the housing and is mounted on the upper portion of the rear wall. The circuit-mounting frame is adapted for mounting a power source thereon, and further has a control circuit mounted thereon. The control circuit is adapted to be connected electrically to the power source.

The fan unit includes a tubular collecting wall mounted on the circuit-mounting frame and disposed above the carrier. The tubular collecting wall has upper and lower wall portions. The upper wall portion has a front side formed with a radial air flow outlet that is registered with the air outlet of the front housing part. The lower wall portion has a fan device mounted therein and connected electrically to the control circuit. The fan device is controlled by the control circuit so as to be adapted to draw aroma of the aromatic preparation on the carrier into the tubular collecting wall and so as to be adapted to blow the aroma inside the tubular collecting wall out of the air outlet of the housing via the radial air flow outlet of the tubular collecting wall.

Preferably, the aroma diffuser further comprises:

slidable frame retaining means, provided on the rear housing part and the circuit-mounting frame, for mounting slidably and removably the circuit-mounting frame on the rear wall, the slidable frame retaining means cooperating with the rear wall to arrest forward and rearward movement of the circuit-mounting frame relative to the rear wall;

upper stop means, provided on the rear housing part, for arresting upward movement of the circuit-mounting frame relative to the rear housing part;

resilient lower stop means, provided on the rear housing part and engaging releasably the circuit-mounting frame, for arresting downward movement of the circuit-mounting frame relative to the rear housing part;

slidable fan unit retaining means, provided on the tubular collecting wall and the circuit-mounting frame, for mounting slidably and removably the tubular collecting wall on the circuit-mounting frame, the slidable fan unit retaining means cooperating with the circuit-mounting frame to arrest forward and rearward movement of the tubular collecting wall relative to the circuit-mounting frame;

upper limiting means, provided on the circuit-mounting frame, for limiting upward movement of the tubular collecting wall relative to the circuit-mounting frame; and resilient lower limiting means, provided on the circuit-mounting frame and engaging releasably the tubular collecting wall, for limiting downward movement of the tubular collecting wall relative to the circuit-mounting frame.

BRIEF DESCRIPTION OF THE DRAWINGS

Other features and advantages of the present invention will become apparent in the following detailed description of the preferred embodiment with reference to the accompanying drawings, of which.

DETAILED DESCRIPTION OF THE PREFERRED EMBODIMENT

Figure 1:
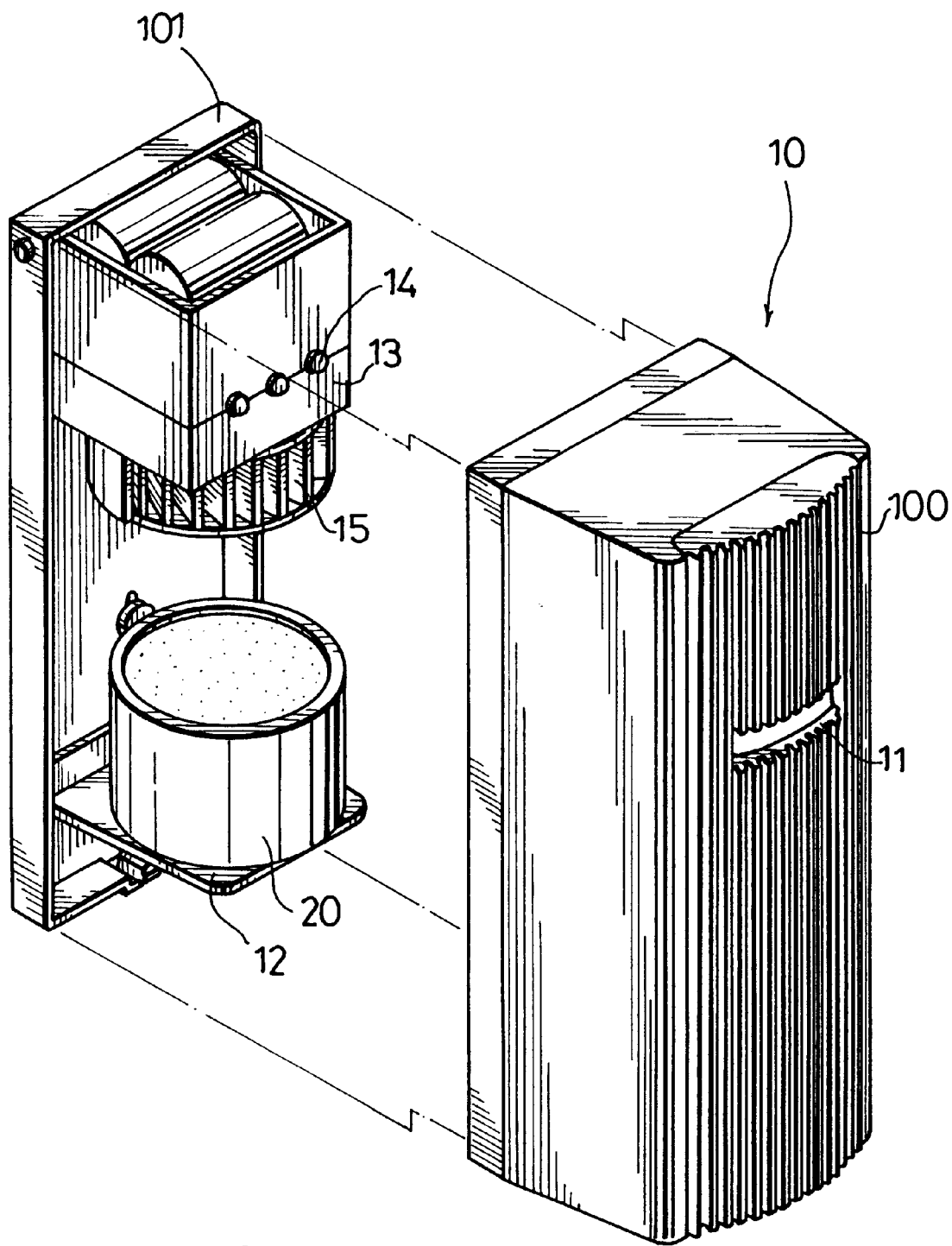
FIG. 1 is a partly exploded perspective view of a conventional aroma diffuser.
Figure 2:
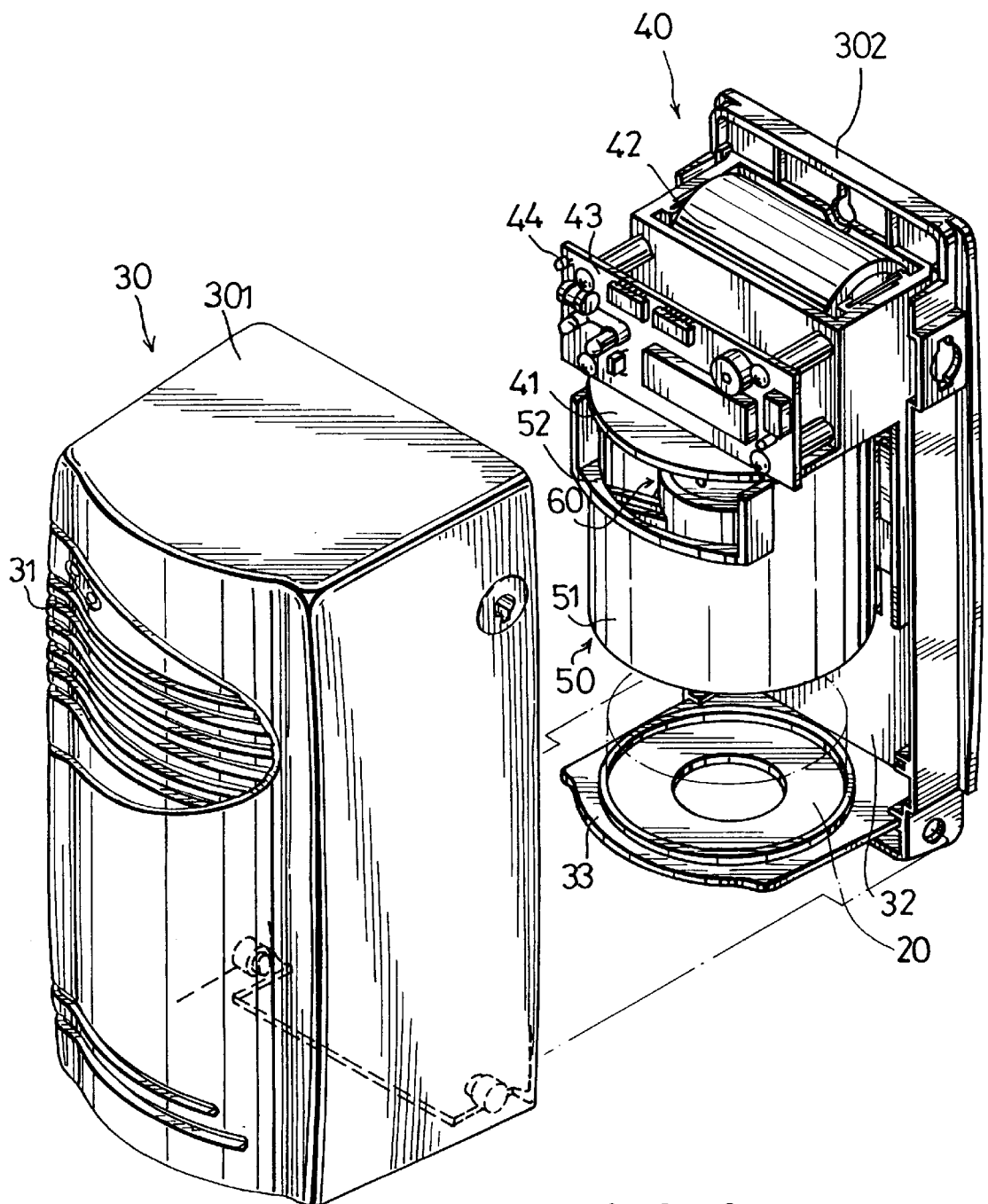
FIG. 2 is a partly exploded perspective view of the preferred embodiment of an aroma diffuser according to the present invention.
Figure 3:
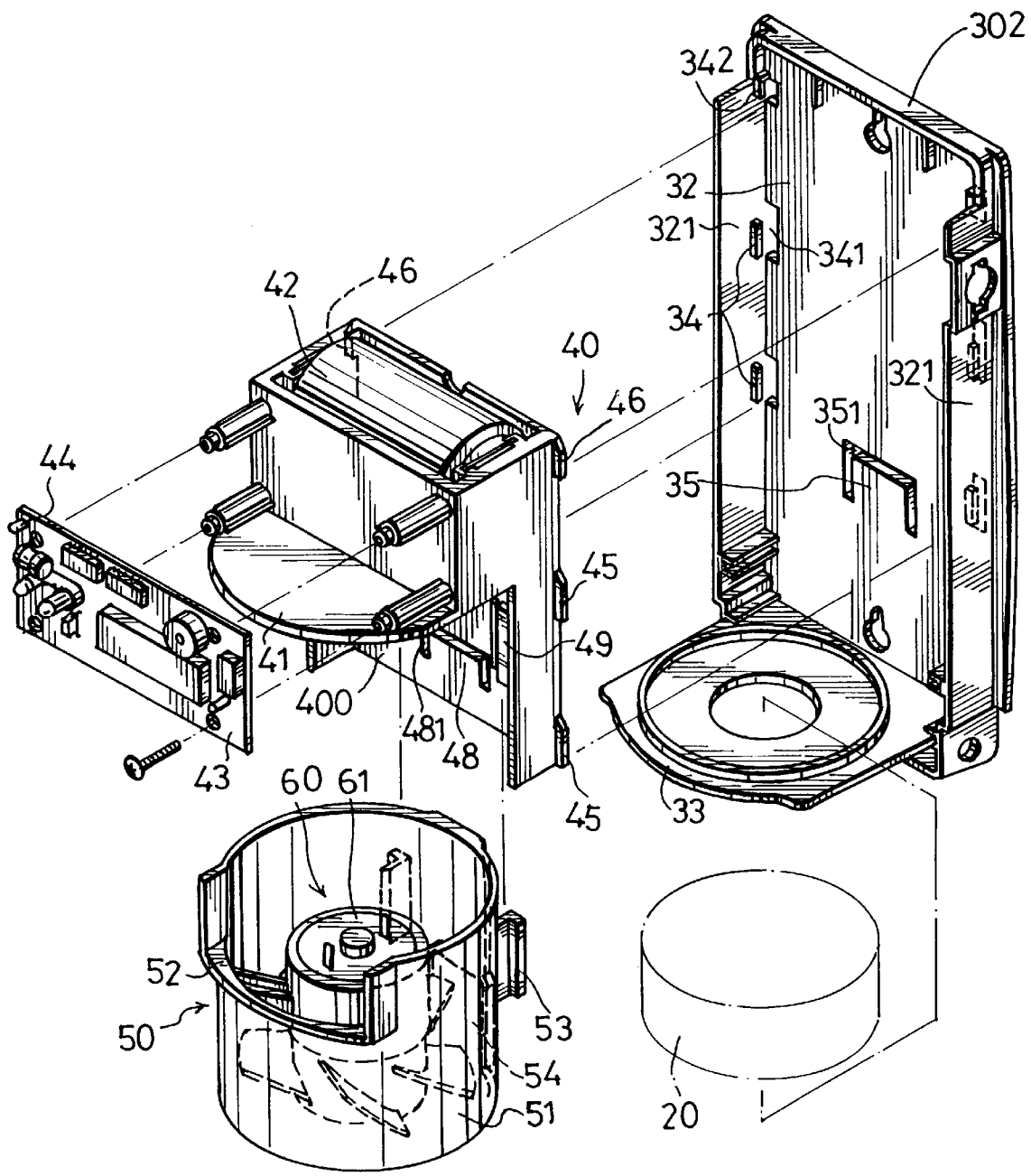
FIG. 3 is a fragmentary exploded perspective view of the preferred embodiment.

Referring to FIGS. 2 and 3, the preferred embodiment of an aroma diffuser according to the present invention is shown to comprise a housing 30, a circuit-mounting frame 40, and a fan unit 50.

The housing 30 has front and rear housing parts 301, 302. The front housing part 301 has an upper portion formed with an air outlet 31. The rear housing part 302 has a rear wall 32 with a carrier 33 that extends transversely into the housing 30 from a lower portion of the rear wall 32. The carrier 33 is capable of supporting an aromatic preparation 20 thereon. The rear housing part 302 further has a pair of side walls 321 that project transversely and respectively from opposite lateral edge portions of the rear wall 32. Each of the side walls 321 is formed with a pair of inward tab projections 34 that are adjacent to an upper portion of the rear wall 32 and that cooperate with the rear wall 32 to define a pair of lateral slide grooves 341 at the lateral edge portions of the rear wall 32. Each of the side walls 321 further has an upper end formed with an upper stop projection 342. The lower portion of the rear wall 32 is further formed with a resilient lower stop projection 35 that projects into the housing 30. In this embodiment, the lower portion of the rear wall 32 is formed with a rectangular opening 351. The lower stop projection 35 is formed as a rectangular stop plate that is disposed in the opening 351 and that has a connecting edge connected to the rear wall 32 at a lower edge of the opening 351, and a stopping edge opposite to the connecting edge. The lower stop projection 35 inclines upwardly and forwardly from the lower edge of the opening 351 such that the stopping edge projects forwardly relative to the rear wall 32. The lower stop projection 35 can be pushed toward the rear wall 32 so as to extend the stopping edge into the opening 351, the purpose of which will be described in greater detail in the succeeding paragraphs.

Figure 4:
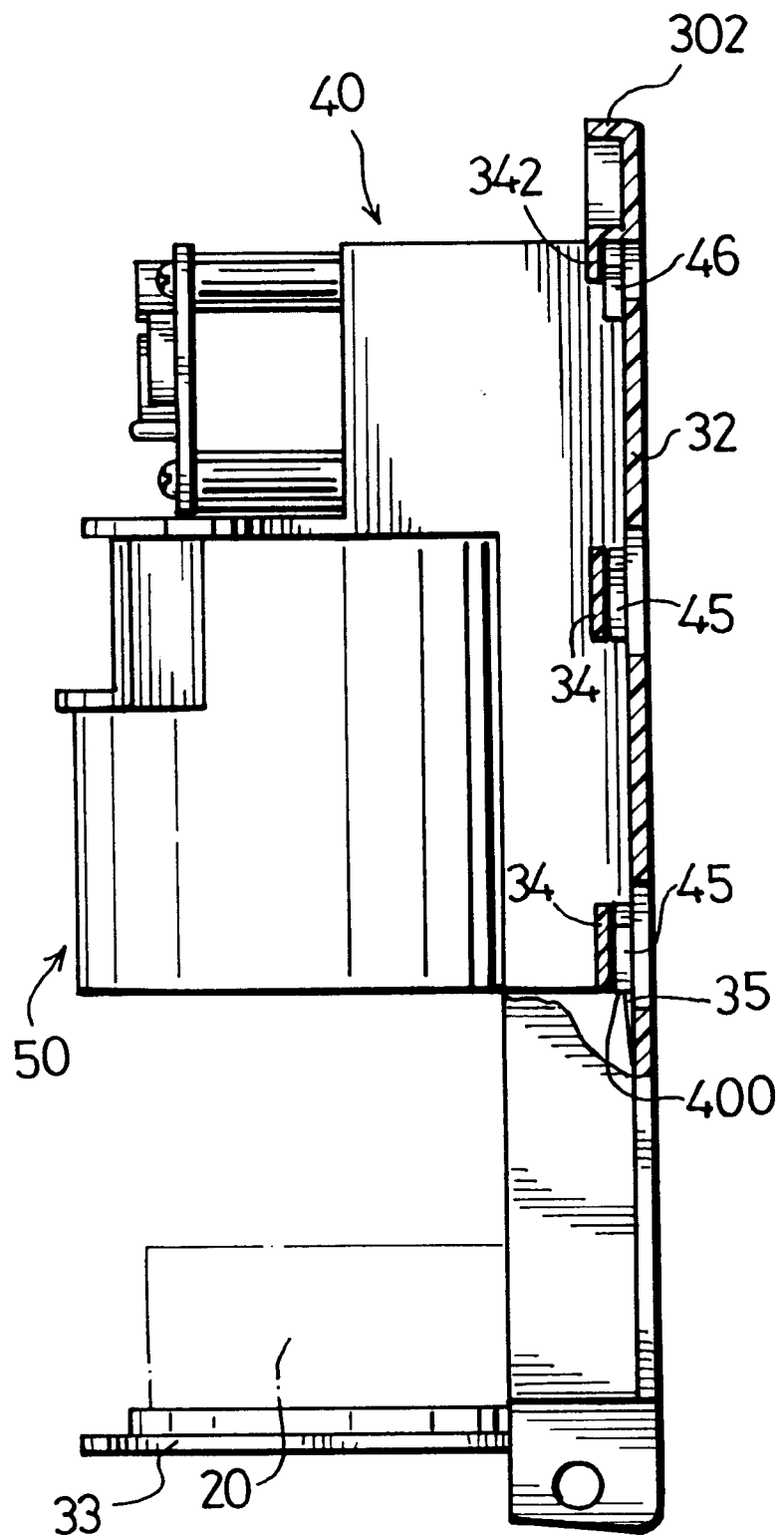
FIG. 4 is a schematic partly sectional view illustrating how a circuit-mounting frame is mounted removably on a housing of the preferred embodiment.

The circuit-mounting frame 40 is disposed inside the housing 30 and includes a back plate 400 mounted on the upper portion of the rear housing part 301. A cover plate 41 extends transversely from the back plate 400. A power source 42 and a control circuit 43 are mounted on a top side of the cover plate 41. The control circuit 43 is connected electrically to the power source 42 and includes a known sensing unit 44, such as an infrared switch or a timer, for automatic or periodic control of the aroma diffuser in a conventional manner. As shown in FIGS. 2, 3 and 4, the back plate 400 has opposite lateral edges formed respectively with a pair of slide lugs 45 that engage slidably the slide grooves 341 and that are retained removably between the tab projections 34 and the rear wall 32 of the rear housing part 302 to arrest forward and rearward movement of the back plate 400 relative to the rear wall 32. The tab projections 34 and the slide lugs 45 cooperatively form a slidable frame retaining unit. The back plate 400 further has a top edge formed with a pair of lateral limit flanges 46 that engage the upper stop projections 342 to arrest upward movement of the back plate 400 relative to the rear housing part 302. The lower stop projection 35 engages releasably a bottom edge of the back plate 400 to arrest downward movement of the back plate 400 relative to the rear housing part 302. The back plate 400 is further formed with a resilient limiting projection 48 that projects forwardly relative to the back plate 400. In this embodiment, the back plate 400 is formed with a rectangular opening 481. The lower limiting projection 48 is formed as a rectangular limit plate that is disposed in the opening 481 and that has a joining edge connected to the back plate 400 at a lower edge of the opening 481, and an engaging edge opposite to the joining edge. The lower limiting projection 48 inclines upwardly and forwardly from the lower edge of the opening 481 such that the engaging edge projects forwardly relative to the back plate 400. The lower limiting projection 48 can be pushed toward the back plate 400 so as to extend the engaging edge into the opening 481, the purpose of which will be described in greater detail in the succeeding paragraphs. The back plate 400 is further formed with a parallel pair of elongated first slide rails 49 on a front side and respectively adjacent to opposite lateral sides of the lower limiting projection 48.

Figure 5:
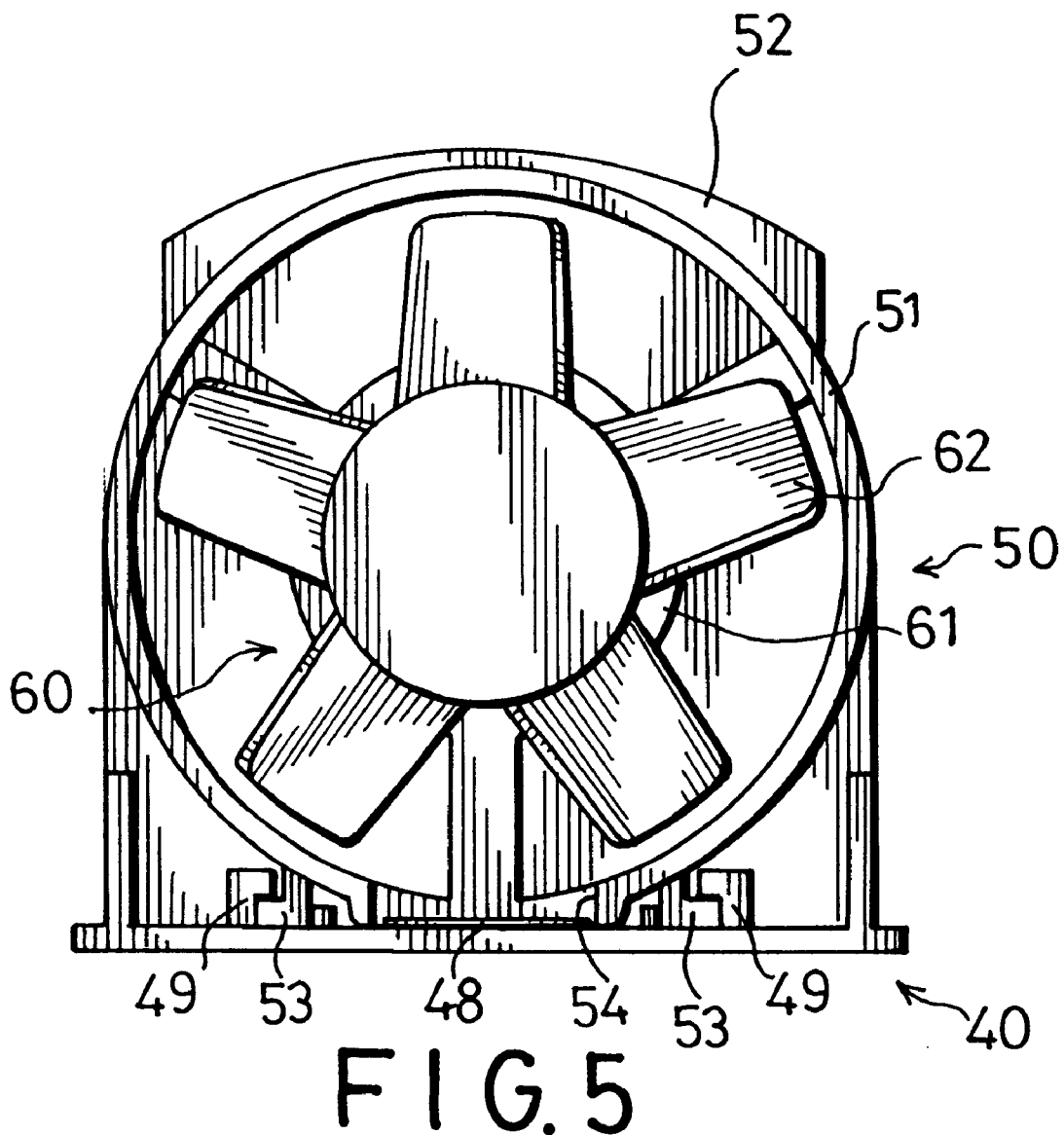
FIG. 5 is a schematic bottom view illustrating how a fan unit is mounted removably on the circuit-mounting frame of the preferred embodiment.

Referring to FIGS. 2, 3 and 5, the fan unit 50 includes a tubular collecting wall 51 with upper and lower wall portions, and a fan device 60 mounted in the lower wall portion of the tubular collecting wall 51. The fan device 60 is connected electrically to the control circuit 43 and includes a motor 61 that drives rotatably a fan blade 62. The upper wall portion of the tubular collecting wall 51 has a front side formed with a radial air flow outlet 52 that is registered with the air outlet 31 of the housing 30. The tubular collecting wall 51 further has a rear side formed with a parallel pair of elongated second slide rails 53 for engaging slidably and removably the first slide rails 49. The slide rails 49, 53 form a slidable fan unit retaining device that cooperates with the back plate 400 to arrest forward and rearward movement of the tubular collecting wall 51 relative to the back plate 400. The cover plate 41 covers the upper wall portion of the tubular collecting wall 51 and acts as an upper limiting device for limiting upward movement of the tubular collecting wall 51 relative to the back plate 400. The tubular collecting wall 51 is further formed with a notch 54 that opens at a bottom edge thereof to permit extension of the lower limit projection 48 therein such that the engaging edge of the lower limit projection 48 engages releasably the bottom edge of the tubular collecting wall 51 at an upper periphery of the notch 54 to limit downward movement of the tubular collecting wall 51 relative to the back plate 400.

During assembly, the fan unit 50 is mounted on the circuit-mounting frame 40 by engaging slidably the second slide rails 53 with the first slide rails 49. When the top edge of the tubular collecting wall 51 abuts against the cover plate 41, the lower limit projection 48 extends into the notch 54 so as to engage the bottom edge of the tubular collecting wall 51 at the upper periphery of the notch 54. Thereafter, the circuit-mounting frame 40 is mounted on the rear wall 32 by extending slidably the slide lugs 45 into the slide grooves 341. When the limit flanges 46 engage the upper stop projections 342, the lower stop projection 35 engages the bottom edge of the back plate 400, and the slide lugs 45 are retained between the tab projections 34 and the rear wall 32. The front housing part 301 can be mounted on the rear housing part 302 in a conventional manner at this time.

In use, the tubular collecting wall 51 disposes the fan device 60 to be adjacent to the aromatic preparation 20 on the carrier 33 to enable the fan device 60 to draw a higher concentration of the aroma of the aromatic preparation 20 into the tubular collecting wall 51. The upper wall portion of the tubular collecting wall 51 is closed by the cover plate 41 so that the aroma can be collected in the tubular collecting wall 51 and is can be prevented from spreading into the housing 30. In response to signals from the sensing unit 44, the control circuit 43 activates the fan device 60 so that the aroma inside the tubular collecting wall 51 is blown out of the air outlet 31 of the housing 30 via the air flow outlet 52 in order to generate a fragrant scent at the vicinity of the aroma diffuser.

To disassemble the aroma diffuser, the front housing part 301 is initially removed from the rear housing part 302. Then, the lower stop projection 35 is pushed toward the rear wall 32 such that the stopping edge thereof extends into the opening 351 and disengages the bottom edge of the back plate 400. The back plate 400 can then be moved downwardly relative to the rear wall 32 until the slide lugs 45 cease to be restricted by the tab projections 34. The circuit-mounting frame 40 can be removed from the rear housing part 302 at this time.

To remove the fan unit 50 from the circuit-mounting frame 40, the lower limit projection 48 is pushed toward the back plate 400 such that the engaging edge thereof extends into the opening 481 and disengages the tubular collecting wall 51. The tubular collecting wall 51 can then be moved downwardly relative to the back plate 400 until the second slide rails 53 disengage the first slide rails 49. The fan unit 50 can be removed from the circuit-mounting frame 40 at this time.

The advantages of the aroma diffuser of this invention are as follows:

1. Due to the presence of the tubular collecting wall 51, loss of aroma inside the housing 30 can be avoided to result in a higher concentration of aroma diffused by the aroma diffuser and in a broader effective scope.
2. The housing 30, the circuit-mounting frame 40 and the fan unit 50 are mounted detachably to one another to facilitate component inspection, repair and replacement.

While the present invention has been described in connection with what is considered the most practical and preferred embodiment, it is understood that this invention is not limited to the disclosed embodiment but is intended to cover various arrangements included within the spirit and scope of the broadest interpretation so as to encompass all such modifications and equivalent arrangements.

I claim:

1. An aroma diffuser comprising:

a housing including front and rear housing parts, said front housing part having an upper portion formed with an air outlet, said rear housing part having a rear wall with an upper portion and a lower portion, said lower portion of said rear wall having a carrier that extends transversely into said housing and that is adapted to support an aromatic preparation thereon;

a circuit-mounting frame disposed inside said housing and mounted on said upper portion of said rear wall, said circuit-mounting frame being adapted for mounting a power source thereon, said circuit-mounting frame further having a control circuit mounted thereon, said control circuit being adapted to be connected electrically to the power source;

a fan unit including a tubular collecting wall mounted on said circuit-mounting frame and disposed above said carrier, said tubular collecting wall having upper and lower wall portions, said upper wall portion having a front side formed with a radial air flow outlet that is registered with said air outlet of said front housing part, said lower wall portion having a fan device mounted therein and connected electrically to said control circuit, said fan device being controlled by said control circuit so as to be adapted to draw aroma of the aromatic preparation on said carrier into said tubular collecting wall and so as to be adapted to blow the aroma inside said tubular collecting wall out of said air outlet of said housing via said radial air flow outlet of said tubular collecting wall;

slidable fan unit retaining means, provided on said tubular collecting wall and said circuit-mounting frame, for mounting slidably and removably said tubular collecting wall on said circuit-mounting frame, said slidable fan unit retaining means cooperating with said circuit-mounting frame to arrest forward and rearward movement of said tubular collecting wall relative to said circuit-mounting frame;

upper limiting means, provided on said circuit-mounting frame, for limiting upward movement of said tubular collecting wall relative to said circuit-mounting frame; and resilient lower limiting means, provided on said circuit-mounting frame and engaging releasably said tubular collecting wall, for limiting downward movement of said tubular collecting wall relative to said circuit-mounting frame.

2. The aroma diffuser as claimed in claim 1, wherein said circuit-mounting frame includes a back plate, said slidable fan unit retaining means including a parallel pair of elongated first slide rails formed on a front side of said back plate, and a parallel pair of elongated second slide rails formed on a rear side of said tubular collecting wall and engaging slidably and removably said first slide rails.

3. The aroma diffuser as claimed in claim 2, wherein said back plate is formed with a rectangular opening having a lower edge, said resilient lower limiting means including a rectangular limit plate that is disposed in said rectangular opening and that has a joining edge connected to said back plate at said lower edge of said rectangular opening, and an engaging edge opposite to said joining edge, said limit plate inclining upwardly and forwardly from said lower edge of said rectangular opening such that said engaging edge projects forwardly relative to said back plate for engaging releasably a bottom edge of said tubular collecting wall.

4. The aroma diffuser as claimed in claim 3, wherein said rear side of said tubular collecting wall is formed with a notch that opens at said bottom edge and that has an upper periphery, said limit plate extending into said notch and engaging said bottom edge of said tubular collecting wall at said upper periphery of said notch.

5. The aroma diffuser as claimed in claim 1, wherein said upper limiting means comprises a cover plate extending transversely from said back plate to cover said upper wall portion of said tubular collecting wall.

6. The aroma diffuser as claimed in claim 5, wherein said control circuit is mounted on a top side of said cover plate, said cover plate being adapted to mount the power source on said top side thereof.

\* \* \* \* \*